United States Patent [19]

Kaine et al.

[11] Patent Number: 4,662,221
[45] Date of Patent: May 5, 1987

[54] METHOD AND APPARATUS FOR MEASURING MATERIAL

[75] Inventors: Eugene Kaine, Orlando; Homer G. Woten; Everett S. Willston, both of Winter Haven, all of Fla.

[73] Assignee: Unisul, Inc., Winter Haven, Fla.

[21] Appl. No.: 770,905

[22] Filed: Aug. 30, 1985

Related U.S. Application Data

[63] Continuation-in-part of Ser. No. 534,327, Sep. 21, 1983, abandoned.

[51] Int. Cl.⁴ .................... G01N 9/24; G01N 29/00
[52] U.S. Cl. .................... 73/599; 73/32 A; 73/861.02; 374/43
[58] Field of Search .............. 73/32 A, 599, 861.02, 73/861.03, 217, 218; 374/43, 44

[56] References Cited

U.S. PATENT DOCUMENTS

| | | | |
|---|---|---|---|
| 1,712,515 | 5/1929 | Norris | 73/599 |
| 2,538,444 | 1/1951 | De Mars | 73/599 |
| 2,768,524 | 10/1956 | Beard | 73/599 |
| 3,925,850 | 12/1975 | Lytton | 73/32 A |
| 3,987,660 | 10/1976 | Pelanne | 374/44 |
| 4,204,432 | 5/1980 | Pujolle et al. | 73/599 |
| 4,481,820 | 11/1984 | Thomann | 73/599 |
| 4,581,935 | 4/1986 | Breazeale | 73/599 |

*Primary Examiner*—Stewart J. Levy
*Assistant Examiner*—John E. Chapman, Jr.
*Attorney, Agent, or Firm*—Lalos, Keegan & Kaye

[57] ABSTRACT

A method and apparatus are disclosed which relate to measuring the quantity and thermal insulating value of fibrous material as it is delivered from a source to another location. A feeder mechanism is provided for delivering the material such as insulation to housing from which it is dispensed ultimately to some cavity such as wall space or surface. The housing includes rotary vanes which divide the housing into a number of separate chambers. A measuring system provided with electronic circuitry and acoustical apparatus delivers a controlled acoustical signal to the chamber containing the fibrous material. A sensor senses acoustical signal generated by a source but altered by the fibrous material within the chamber. Signals corresponding to the source signal and the sensed signal are both fed to a comparator which in turn emits a signal proportional to the volume and density, or thermal insulating value of material contained in the chamber.

65 Claims, 6 Drawing Figures

METHOD AND APPARATUS FOR MEASURING MATERIAL

This application is a continuation-in-part of copending application Ser. No. 534,327, filed on Sept. 21, 1983, now abandoned.

BACKGROUND AND DISCUSSION OF THE INVENTION

In providing insulating materials for wall space within the walls of residential and commercial buildings, and also the attic space of buildings, in the past it has been difficult to measure the actual amount of material delivered to the space. The insulating material is typically in fiber form and contained in bags at the time of delivery to the building site requiring insulation. Although one can be sure of the amount of material in a particular bag, verification of the amount actually sprayed into the wall or attic space, to insure that the consumer has obtained what he purchased, has been difficult at best. The problem in measuring the flow of such fibrous materials has been that the density can change. Although the volume flow can be measured, it is often difficult to relate volumetric flow rate to the actual quantity of fibrous material delivered to the wall since the density of the material can be varied significantly.

The invention described herein has overcome the problems in measuring fibrous material, and in particular, insulation used for insulating wall space. The invention relates to a system for accurately measuring the amount of fibrous material delivered by providing compensation for variation in density of the material as well as changes in volume flow rate. More specifically, the invention relates to the use of an acoustic signal generated in combination with an acoustical sensor and a comparator for comparing the signal generated with the signal received from the sensor to determine the amount of material in a given chamber. The acoustical generator such as a loudspeaker is placed at one end of a housing while the microphone or other acoustical sensing means is displaced relative to the loudspeaker at another portion of the housing so that chamber of material can pass between them. Chambers having insulating material for delivery to the wall space are then moved past the speaker and microphone assembly. The speaker is activated by a source signal to generate an acoustical signal to the successive chambers as they pass between the speaker and microphone. The microphone senses the acoustical wave generated as modified by the material in a given chamber and generates a corresponding electrical signal to a computer which then computes the relationship between the source signal and the sensed signal to produce a signal corresponding to the volume and density of material in the chamber. The computer can then sum the measurements for each chamber, such that a running tabulation of the amount of material being delivered can be obtained.

In another embodiment of the invention, the measuring apparatus simply measures the "R" factor rather than the quantity or density or some other parameter of material. The "R" factor is the insulating value of a given material. It has been learned that the "R" factor of a material is directly related to a sound attenuation. By applying this relationship to the audio measuring apparatus and other elements of the system, one can measure the "R" of a material being delivered to a cavity for insulation quite readily without resort to additional parameters such as the type of material employed and additional computations to adjust quantities to the alternate "R" factor which is typically the factor most desired.

It has been determined that different insulator materials attenuate sound at different rates. For example, rock wool is about 6.5 db/ounce, glass wool is about 12 db/ounce, and cellulose fiber is about 7.2 db/ounce. In checking the charts that all wool manufacturers are required to print on every bag of wool regarding the coverage or per square foot yield based on pounds, it has been computed that rock wool's typical "R" value per ounce is about 1.34. Glass wool is about 2.4 r/ounce and cellulose is about 1.42 r/ounce. That produces a direct relationship between db or audio attenuation and "R" factor for the material being measured. The advantage of using a system for simply measuring the "R" factor is that one need not make special consideration for different materials. Rather regardless of the material, their "R" value can be readily measured without adjustments in the system. The advantage of such a system is when the insulator appears at a location and must change the type of insulation employed. In other systems, this may create a problem requiring further computation. With the system using the relationship between audio attenuation and "R" factor, one can simply add new material in lieu of the old material and have the system continue to measure the "R" factor of the material being used as a fill for wall space or other area of a building.

Another advantage of having a metered system and particularly one which prints out the amount of "R" factor being delivered is that the opportunity for misrepresenting the amount of material delivered to a particular location is substantially impaired. Certain state authorities have been attempting to find ways to insure that insulators around the country are not misrepresenting the amount of insulation they deliver and thereby overcharge the customer. A fool proof or at least largely fool proof system has been sought to avoid fraud or other misuse to customers purchasing insulation. By using a system that simply measures the "R" factor, which avoids computation and a chance for misrepresentation, the customer can be assured that he has received the amount of material he has purchased. When a fool proof measuring system such as the one described herein is used, it becomes easier for inspection and other regulatory agencies to determine whether insulators or other vendors are delivering the requisite amounts of insulation.

In addition, by adopting the system that uses an audio frequency for measuring "R" factor, inspection of an in situ situation is made much easier. To measure the "R" factor of insulation in place, the cookie cutter approach typically has been used. This approach requires the operator to crawl between the joist in the flooring using instruments to cut through the wool or other insulating material and actually withdraw it from its in situ position for measuring. This system is cumbersome, dangerous to the operator and provides the opportunity for damage to the building if not conducted properly. By using a system that employs an acoustical mechanism and relates attenuation to the "R" factor, these problems can largely be overcome.

A system employing a sound attenuation can use a sound generator having a source which constantly produces the sound and a system which compensates for changes in the sound due to external factors. Another system which can be employed and one which eliminates a certain amount of electronics is the use of a pulse system in which a single pulse is generated over a given period of time.

With a pulse system an impulse generator is connected to an audio transducer to change the electrical signal to the audio signal used within the chamber. The attenuated audio signal is then transformed to an electrical signal, converted to a digital signal and delivered to a computer for additional computation. An LCD or printer is connected to the computer to permit a visual display of "R" value data corresponding to the signal sensed. The computer also controls the impulse generator and peak detector to insure they they are operated in the proper time sequence with regard to the chamber being measured. Various voltage converters can be employed to accommodate a fixed power source with the various elements in the system.

The advantage of this system is the avoidance of interference and other problems associated with other audio devices. The additional circuitry and other absorption systems as described above are simply not needed. Also by relating the output directly to "R" value, and the computer being properly programmed, the correct amount of insulation can be chosen for a given area. After delivery is completed a computer printout can be provided to the customer as a receipt verifying the amount actually delivered.

The above has been a general description of some of the problems which have been involved in measuring the delivery of fibrous materials and some advantages of the invention described herein. Other advantages will become apparent from the detailed description of the preferred embodiment which follows.

DETAILED DESCRIPTION OF THE PREFERRED EMBODIMENT

Figure 1:
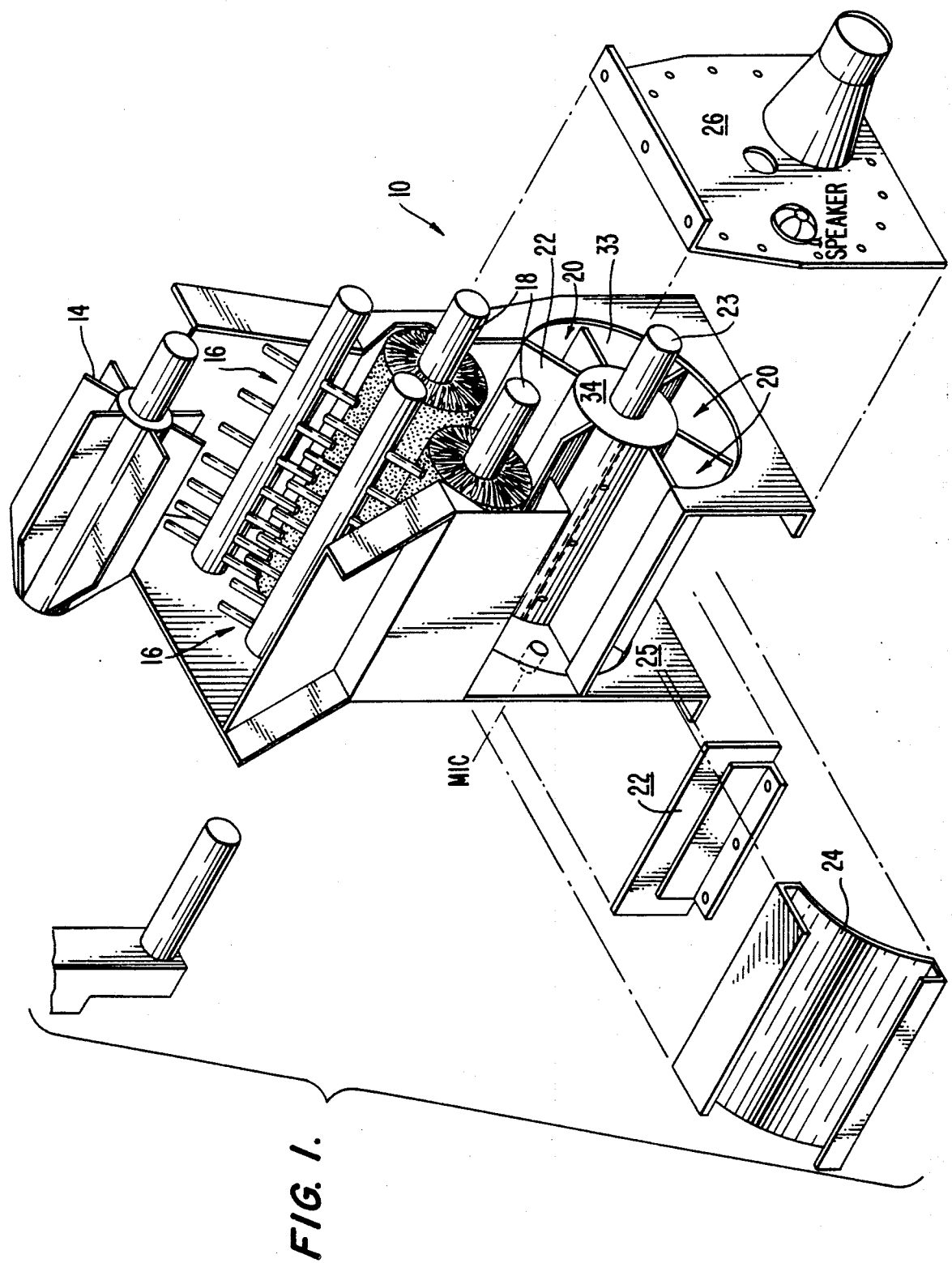
FIG. 1 is an exploded view of part of a hopper and delivery assembly for delivering fibrous materials such as insulation.

It can be seen in FIG. 1, the apparatus for delivering fibrous material to wall space or other cavity includes a housing 10 which contains various rotating equipment and an air lock feeder for propelling material in successive chambers out of the housing through a port and ultimately through a hose to the space to be filled. For the purposes of discussions of this particular embodiment, a number of elements of the equipment such as the power source for rotation and other details for delivering the fibrous material to the housing will not be discussed in depth. For the purposes of this embodiment the discussion of the housing and the equipment contained therein will be described primarily in conjunction with the measuring apparatus. The details of the power source and rotative equipment are shown and described in copending application U.S. Ser. No. 426,160, filed on Sept. 28, 1982, incorporated herein in its entirety by reference.

The housing 10 includes an agitator 14 which receives the fibrous material from a hopper as it is delivered to the hopper from a package or some other delivery means. Beneath agitator 14 there are provided counter rotating shredders 16 which receive material from the agitator and provide initial shredding to achieve uniformity and density of the fibrous material before delivery to other elements of the apparatus. Positioned immediately below the counter rotating shredders 16 are tearing and separation brushes 18 which also counter rotate to tear apart the fibrous material delivered thereto. The last stage in the delivery system includes a drum 34 from which extends a number of vanes 22 for rotation in a cylindrical housing 33. The vanes in combination with drum 34 and housing 33 provide a number of chambers 20 which are rotatable about axis of shaft 23 supporting drum 34. Shaft 23 is supported by two opposed end plates 25, 26 arranged generally perpendicular to the axis of shaft 23 and parallel to the path of rotation of vanes 22. As the chambers are rotated about the axis of shaft 23 into communication with the tearing and separating brushes 18, the material having passed through this latter stage is delivered to the successive chambers as each chamber 20 is exposed to the interface between the two brushes.

Figure 5:
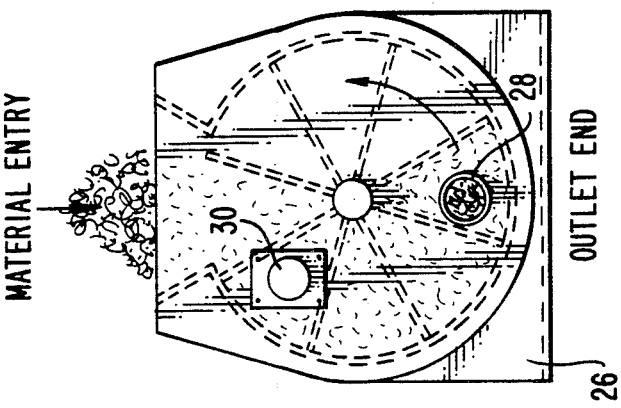
FIG. 5 is an outlet end view of the system shown in FIG. 1.
Figure 4:
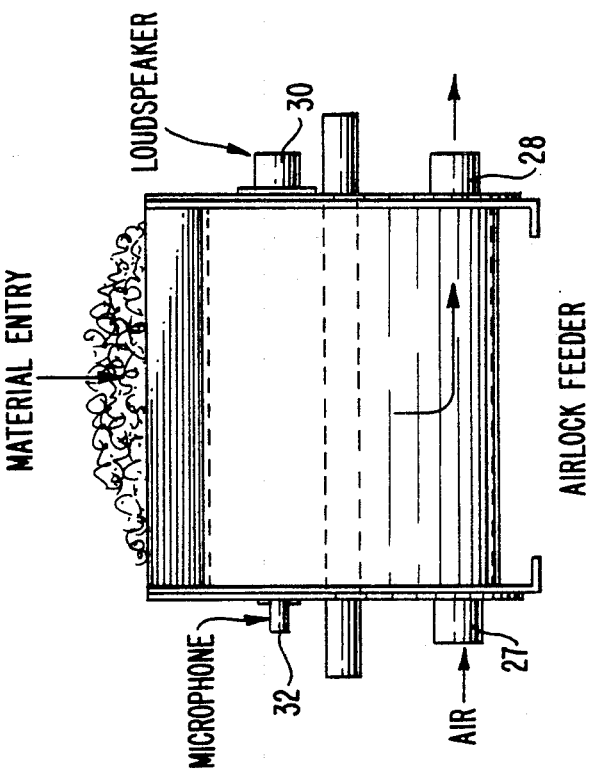
FIG. 4 is a side view of the system shown in FIG. 1.
Figure 3:
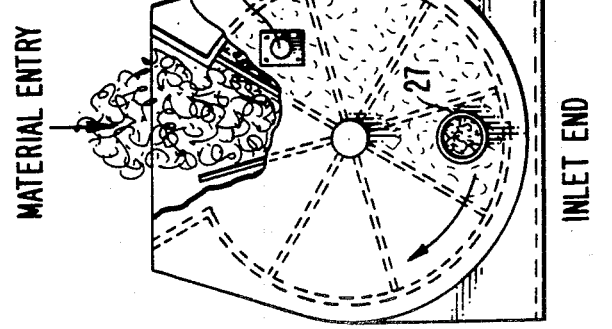
FIG. 3 is an end view of an inlet end of the delivery system shown in FIG. 1.

An air lock delivery system operates in conjunction with chambers 20 defined by the vanes, an inlet port 27 and exhaust port 28 to eject and deliver the material contained in the chambers through a hose (not shown), ultimately to the space to be filled. As can be seen in FIGS. 3, 4 and 5, inlet port 27 is located on plate 25 and exhaust port 28 on end plate 26 in a co-linear relationship. Air or some other compressible fluid under pressure is delivered to inlet port 27 and exposed to the pressurized fluid, the material contained within chamber 20 is forced by the pressurized air out of the chamber through exhaust port 28. A flexible hose or other delivery means is connected to exhaust port 28 for actually directing the material forced out of chambers 20 into or onto the wall space or other cavity to be filled.

Utilizing this delivery system, a measuring apparatus is employed to measure the amount of material in each chamber as it passes a given point in rotating through the arcuate path to the airlock feeder where the fibrous material is removed from the chamber as part of the delivery operation. As can be seen in FIGS. 3, 4 and 5, the system includes a loudspeaker 30 mounted on end plate 26 with microphone 32 mounted on the opposite end plate 25 and generally co-linear with loudspeaker 30 along the line parallel with the axis of rotation of the drum 34. In this way, audio signals imparted by loudspeaker 30 travel entirely through the chamber 20 along a longitudinal path coextensive with the vanes 22 to the microphone 32. The signals received by microphone 32 are, of course, modified by the fibrous material contained in the chamber. It has been found that volume of fibrous material will absorb some of the acoustic power generated by loudspeaker 30. The percentge absorbed is proportional to the volume and density of the material in the chamber and appears to revolve around the following relationship:

$$(P^1/P^2) = K_1 e^{K_2 w}$$

P1 and P2 are measurements in the operating system relating to the power input and the power output respectively. $K_1$ is a transmission factor which is a function of transducer efficiency, chamber acoustics and any fixed scaling in the electronics. $K_2$ is the attenuation factor of the fibrous material and varies with frequency. It is determined experimentally. W is the weight of the material. In this machine $P^1$ and $P^2$ are input quantities to the computation so that the logarithmic conversion is a necessary intermediate step. Specifically, the formula employed in converting the parameters to a signal corresponding to volume of material is delivered is as follows:

$$W = \frac{\text{Log}\frac{P_1}{P_2} - \text{Log} K_1}{K_2}$$

The measurements produced are a flow "rate" in ounces per chamber. The flow must be integrated over all of the chambers cycled while the machine is delivering fibrous material to arrive at the sum of ounces representing total delivery.

Figure 2:
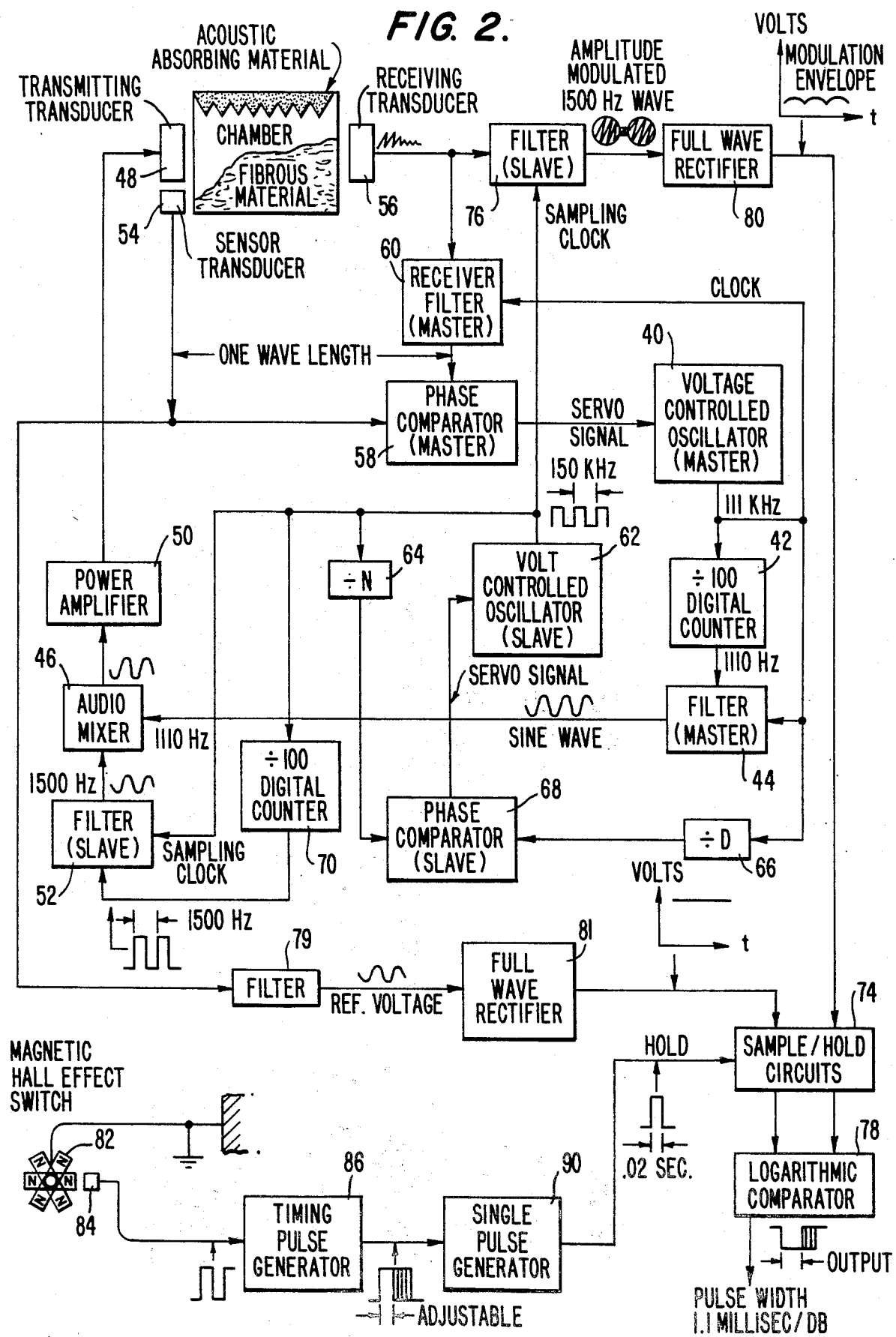
FIG. 2 is a schematic of a circuit diagram of the fibrous material measuring system of the invention.

The system for accomplishing this is shown in FIG. 2. The sound waves reflect back and fourth between the two ends and any instantaneous measurement at the microphone is the sum of the latest wave arriving and several old reflections—an interference pattern of the waves. The interference pattern causes the received signal to reinforce or interfere in such a way as to present two difficulties in measuring repeatable receiver signals for acoustic absorptions less than 6 DB. The output does not follow the pure logarithmic relationship already found in the material for absorptions less than 6 DB. A partial remedy to these two difficulties is to install a permanent acoustic absorbing material in each chamber of at least 6 DB. The interference pattern has the strongest reflected components when the chamber has the lowest absorption.

It is important to have a repeatable ratio of input signal to output signal for an empty chamber in order to establish a measurement baseline. Maintaining the same interference pattern requires maintaining the same wavelengths relative to the chamber length. Changes in air temperature require changes in driving frequency to accomplish this goal. A servo loop which causes a master oscillator to adjust frequency such that the chamber always has a phase change of 360 degrees from end to end provides a reference for such a stabilization. The actual measurement wavelength is shorter and is always a selected ratio to the master wavelength. The two signals are added algebraically and presented to the chamber simultaneously.

The system for accomplishing this is shown in FIG. 2. A master oscillator 40 generates a square wave which is filtered to extract a sine wave. As shown the frequency of the square wave generated by master oscillator 40 of about 111 KHz is divided by digital Counter 42 to generate a signal at 1110 Hz to master filter 44 to extract the sine wave. A signal from master voltage controlled oscillator 40 acts as a sampling clock for master filter 44. The sine wave is added to other signals in the audio amplifier 50. The signals received by audio mixer 46 include the sine wave at 1110 Hz from master filter 44 and a sine wave at 1500 Hz from slave filter 52. The resultant signal generated by mixer 456 is amplified by power amplifier 50 for driving transducer 48. To produce the 1500 Hz sine wave, slave filter 52 receives a sampling clock signal from slave voltage controlled oscillator 62. The same signal is divided by digital counter 70 to produce another square wave signal to slave filter 52 at about 1500 Hz.

A sensing transducer 54 samples the emissions from transducer 48 for phase comparison against the signal from receiving transducer 56 via the receiver master filter 60. Master receiver filter 60, employing the output signal from voltage controlled oscillator 40 as a sampling clock, filters the signal from receiving transducer 56 before delivery to master phase comparator 58 where the signal is compared to that from sensor transducer 54. Any deviation from a predetermined phase relationship is applied as a servo signal from comparator 58 to a master voltage controlled oscillator 40 causing it to change frequency in a direction to minimize the phase error.

In the slave circuit, slave voltage controlled oscillator 62 has its output divided, by a digital counter 64, by an integer N. The master voltage controlled oscillator 40 has its output divided, by digital counter 66, by an integer D. The phasing of signals from two counters 64, 66 is compared in slave phase comparator 68. An error signal produced by comparator 68 drives slave oscillator 62 into phase lock in which its frequency is N/D times that of the master voltage controlled oscillator 40. Full wave rectifier 80 is connected to slave filter 76 to rectify the modulated signal produced by slave filter 76. A sample-hold circuit 74 is connected to full wave rectifier 80 and a full wave rectifier 81, the latter in turn being connected to the output of sensor transducer 54 through filter 79.

In this manner, the sample-hold circuit 74 receives signal corresponding to that delivered to the transducer 48 as well as a signal corresponding that that generated at receiving transducer 56. Slave filter 76 is connected to receive the output of receiving transducer 56 and a signal from slave voltage controlled oscillator 62 as a sampling clock. Full wave rectification of the filter 76 output results in a low frequency voltage whose strength varies with the amount of material and the angular alignment of chambers 20 relative to the transducer. The voice coil voltage is a full wave rectified to provide a reference signal to logarithmic converter or comparator 78. The logarithmic comparator 78 is connected in series with the sample-hold circuit 74 to convert the signals delivered thereto during a given time period into a signal which corresponds to the volume of fibrous material in the chambers 20.

A synchronous timing mark is delivered to sample-hold circuit 74 to activate the hold circuit such that the samples are measured only during a preselected time period. In this particular embodiment a cam activated switch in conjunction with a number of pulse generated circuits are employed to provide pulses during a preselected time sequence to the time holding circuit 74. As can be seen in FIG. 2, the system includes a magnetic hall effect switch 82, in conjunction with the sensor 84 for generating electrical signal which is generally a square wave.

A timing pulse generator 86 is connected to receive the square wave signal from magnetic hall effect switch 82 to generate a pulse to a single pulse generator 90. The timing pulse generator 86 is adjustable to control the width of the pulse generated which in turn controls the timing sequence of single pulse generator 90. The single pulse generator 90 is connected to trigger sample-hold circuit 74 which in turn generates the signal for measurement by the logarithmic comparator during the preselected time period of the pulse so delivered by the single pulse generator 90.

In other words, the pulse generator 90 delivers pulses of fixed duration, but the timing for triggering pulse generator 90 is controlled by pulse generator 86. In this manner, single pulse generator 90 imparts a signal to the sample-hold circuit 74 to hold the signals received from full wave rectifier 80 and full wave rectifier 81 for preselected time or pulse duration for use by the logarithmic comparator 78 to measure the samples held and ultimately generate signal corresponding to the volume of fibrous material in the chamber sensed during the pulse duration.

In operation, drum 34 is continuously rotated to receive fibrous material delivered through the interface of the tearing and separating brushes 18. With continuous rotation, succeeding chambers 20 are moved past the speaker 30 and the microphone 32 before being delivered to the air lock feeder system. During this movement the speaker 30 transduces the electrical signal delivered thereto by the master oscillator 40 to mechanical movement inside the chamber. The fibers within the chamber are set into motion which returns little or no energy to the source. The microphone transduces the sound pressure generated from within chambers 20 to an electrical signal which contains 1500 Hz components along with frequency components generated by movement of the machinery. The filter 76 passes 1500 Hz waves whose amplitude is modified by the varying absorption of the acoustic power by varying amounts fibrous material. Both the filter output 76 from the microphone 32 is rectified and the voice coil voltage is rectified to produce a reference signal for logarithmic converter or comparator 78.

Before being delivered to the comparator 78 the signals are held in a sample-hold circuit 74. Switch 82 provides a synchronous timing mark which is delayed by a timing pulse generator 86 whose pulse width is adjusted by manual control. The trailing edge of the pulse provided by timing pulse generator 86 triggers single pulse generator 90 which generates a pulse of fixed 0.02 seconds duration. The pulse is positioned in time so that the sampling circuit may hold the sample acquired at the beginning of the 0.02 second. The logarithmic converter 78 generates a pulse whose duration is related to the ratio of the two full wave rectifier voltages delivered to the sample-hold circuit 74 at the time that a sample was held. Specifically, the pulse duration is proportional to the logarithm of the ratio of the two voltages.

The measurements of flow rate in ounces per chamber are integrated over all of the chambers cycled while the machine is delivering fibrous material to arrive at the sum of ounces representing a total delivery. The circuitry for rendering such a summation is not shown or disclosed in this embodiment but is well known to those skilled in the art and could be readily integrated to provide a running summation of the material cycled past loudspeaker 30 shown as transducer 48 in FIG. 2 and microphone 32 shown as receiving transducer 56 in FIG. 2.

Figure 6:
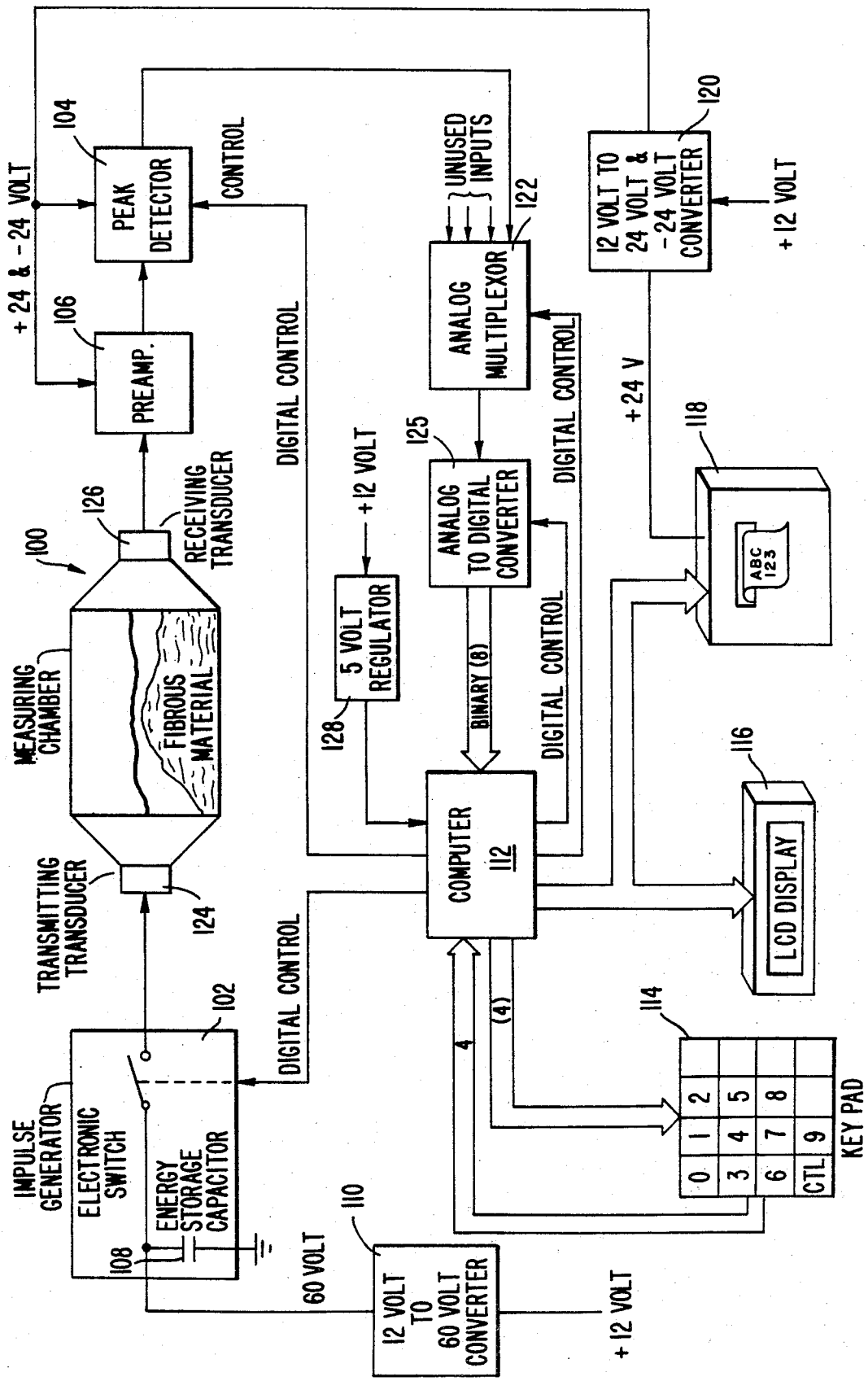
FIG. 6 is a schematic of a circuit diagram of another embodiment of the invention.

A specific embodiment of a system which can be employed to measure the R factor is shown in FIG. 6. Similar to the embodiment of FIG. 2, the embodiment of FIG. 6 includes a measuring chamber 100 corresponding to one of the chambers 20 shown in FIG. 1. The transmitting transducer 124 and receiving transducer 126 of FIG. 6 correspond to the microphone and speaker, respectively, shown in FIG. 1. From the block diagram shown in FIG. 6 it can be seen that an impulse device is employed to measure the quantity of fibrous material in a chamber rather than the constant signal device which has been employed in the embodiment discussed above. As a result the electronic apparatus required to measure the system is simplified without undue loss in accuracy.

More specifically the impulse generator 102 includes an energy storage capacitor 108 which is connected in series to a 60 volt converter 110 which is in turn connected to a 12 volt source. With this system the capacitor 108 can be charged and remain charged until deenergized by the computer 112. A switch 111 for this purpose is included within the impulse generator 102 and operated by the computer 112 to discharge the capacitor at a given time for imparting the impulse to the chamber being measured. A transmitting transducer 124 is connected between impulse generator 102 and measuring chamber 100 for converting the electrical signal to an audio signal which is directed through measuring chamber 100 carrying fibrous material. Receiving transducer 126 senses the acoustical wave generated as dampened by the material in a given chamber and generates a corresponding signal for delivery to computer 112. This is accomplished by amplifying the signal from receiving transducer 126 through a pre-amplifier 106 for use by a peak detector 104 which measures the maximum level of the signal. Once the peak signal is detected a corresponding signal is delivered to an analog multiplexer 122 which is controlled by computer 112. The signal for multiplexer 122 is in turn delivered to an analog digital converter 125 which converts the analog signal into a digital signal of standard binary code for use by the computer. Computer 112 is also connected to the peak detector 104 and the impulse generator 102 to control the timing sequence in the operation of these devices. At a given moment or position of the measuring chamber, electronic switch 111 is closed and storage capacitor 108 is deenergized to create the impulse. Similarly, peak detector 104 is controlled to operate during a certain sequence corresponding to that of the operation of impulse generator 102. In a similar manner computer 112 is connected for control purposes to analog digital converter 124 and analog multiplexer 122 as can be seen to control the operation of these units within a given time sequence.

Computer 112 is also connected to a key pad 114 in such a manner that a scanning technique is employed to determine which key has been depressed. For the purpose of displaying information which has been inputted into the computer or the computer output the computer 112 is connected to an LCD display 116 as well as a printer 118. The computer 112 is programmed to require certain information in measuring the amount of fibrous material (in units of R value) being delivered to a specific location. The previously determined relationship between R value and audio attenuation is programmed into the computer as well as the total amount of insulation (in units of R value) required by the purchaser. Once the requisite amount of insulation has been delivered that amount will be printed on a receipt from printer 118 so that the purchaser will have a reliable indication of the amount of insulation purchased. To arrive at the sum of R values representing a total delivery, the measurements of R value per chamber are integrated over all the chambers cycled while the machine is delivering fiberous material. The circuitry for providing a summation is not specifically disclosed but it is well known to those skilled in the art that a computer can easily be programmed to keep a running total of values. Computer 112 can be programmed to keep a running summation of the R values of material cycled past transmitting transducer 124 and receiving transducer 126. This total can be printed on printer 118 to provide the purchaser with a reliable indication of the total R value of the insulation material purchased.

It should be noted that in the operation of this system a plus or minus 24 volt source is required. For this purpose a 12 volt to 24 volt converter 120 is employed between the printer an the preamp 106 and peak detector 104. For the computer 112 a 5 volt regulator 128 is employed to convert the 12 volt source to a 5 volt input typically used by a computer of this type.

The above has been a detailed description of the preferred embodiment of applicant's invention. Other modification changes can be made without diverting from the full scope of applicant's invention which is set out in the following claims. These claims should be interpreted to include all substantial equivalents of the invention.

What is claimed is:

1. An apparatus for measuring the quantity of a material comprising:
   (a) a series of chambers;
   (b) source means for generating an acoustical signal;
   (c) sensing means arranged at a station opposite said source means for sensing acoustical signals generated by said source means, said sensing means including means for generating a sensed electrical signal corresponding to the magnitude of the acoustical signal sensed by said sensing means;
   (d) means for moving said series of chambers past said station between said sensing means and said source means;
   (e) means for generating a reference signal indicative of the generated acoustical signal;
   (f) measuring means for receiving said sensed electrical signals from said sensing means including a comparator for comparing said reference signal with the sensed signal from said sensing means and generating a signal corresponding to a quantity of material within each of said chambers.

2. The apparatus according to claim 1 wherein said reference signal generating means comprises a source electrical signal means for generating a source electrical signal responsive to said generated acoustical signal, said comparator including means for receiving said source electrical signal and comparing said source electrical signal received with the electrical signal generated by said sensing means and generating said signal corresponding to the quantity of material within said chamber.

3. The apparatus according to claim 2 wherein said comparator is a logarithmic comparator which generates the signal proportional to the logarithm of the ratio of signals corresponding to the source signal and the sensed signal.

4. The apparatus according to claim 3 wherein said source means for generating an acoustical signal includes an oscillating means for delivering a source signal at a preselected frequency, a first transducer for transducing the source signal to mechanical movement within the chamber.

5. The apparatus according to claim 4 wherein said first transducer means includes a loudspeaker communicating with said chamber.

6. The apparatus according to claim 5 wherein said sensing means includes a second transducer for transducing sound pressure to said sensed electrical signal.

7. The apparatus according to claim 6 wherein said second transducer includes a microphone.

8. The apparatus according to claim 7 wherein said source means for generating an acoustical signal includes a source providing a square wave signal, a source filter for receiving a square wave signal and generating a sine wave proportional to the square wave signal received.

9. The apparatus according to claim 8 wherein said source means further includes a power amplifier for amplifying the sine wave signal generated by said source filter.

10. The apparatus according to claim 9 further comprising a sensor filter for receiving a signal from said sensing means and modulating said signal for delivery to a rectifier.

11. The apparatus according to the claim 10 wherein the said source electrical signals are filtered and rectified.

12. The apparatus according to claim 11 further comprising a pulse generating means for generating pulses of a fixed duration, holding circuit means for holding signals received thereby at the beginning of the fixed duration of pulses generated by said pulse generating means, said holding means having means for receiving sensed signals and source signals and delivering said signals to said comparator during the fixed time duration of pulses generated by said pulse generating means.

13. The apparatus according to claim 12 wherein said pulse generating means includes means for providing synchronous timing signal to said holding circuit means and a switch operated at preselected intervals to generate a signal corresponding to the operation of the switch.

14. The apparatus according to claim 13 wherein a timing pulse generator is integrated between the switch and the single pulse generator for generating a pulse of a width corresponding to the pulse received from said switch and delivering said pulse to said single pulse generator, the width of the pulse being generated and delivered to the single pulse generator being adjustable to control the timing of the fixed duration pulse generated for activating the holding circuit means.

15. The apparatus according to claim 14 further comprising means for adjusting the source means signal to achieve a preselected phase change within the chamber.

16. The apparatus according to claim 15 wherein said means for adjusting the source means signal includes a base comparator for comparing signals at said source means and at said sensing means for phase comparison and emitting a signal to said source electrical signal means to minimize phase change.

17. The apparatus according to claim 1 wherein said series of chambers are arranged for movement along a closed path.

18. The apparatus according to claim 17 wherein said chambers arranged for movement along a closed path are arranged circumferentially about a single axis of rotation.

19. The apparatus according to claim 18 further comprising delivery means for delivering material to be measured to said chambers as they are moved about the said closed path, said delivery means being arranged upstream of said station.

20. The apparatus according to claim 19 wherein said chambers include vanes extending radially from a shaft, and said vanes being equally spaced about said shaft to form chambers of equal volume, said shaft with said vanes being arranged for rotation within a housing, and said station being fixed to said housing with the vanes being movable past said station about said axis of rotation.

21. The apparatus according to claim 20 wherein said housing includes two spaced apart plates between which the vanes on the shaft rotate, said sensing means and said source means being secured to said end plates generally opposite one another.

22. A method for measuring the quantity of material in a chamber comprising:
 (a) providing a station for delivery of fiber material;
 (b) arranging a series of chambers for movement past said delivery station to receive said fiber materials being delivered thereby;
 (c) moving said chambers having been filled with fiber material past a second station;
 (d) at said second station generating an acoustical signal within each chamber passing thereby;
 (e) sensing the acoustical signal from within each said chamber;
 (f) delivering a sensed electrical signal corresponding to the magnitude of the acoustical signal sensed;
 (g) generating a reference signal indicative of the generated acoustical signal; and
 (h) measuring the sensed signal by comparing said reference signal with the sensed signal and generating a signal corresponding to a quantity of material within each said chamber.

23. The method according to claim 22 further comprising generating a source electrical signal corresponding to said acoustical signal, said measuring step including receiving said source electrical signal and comparing said source electrical signal received with the electrical signal generated of said sensing step and generating said signal corresponding to the quantity of material within said chamber.

24. The method according to claim 23 wherein said measuring step includes generating a signal proportional to the logarithm of the ratio of signals corresponding to the source signal and the sensed signal.

25. The method according to claim 24 wherein said step for generating an acoustical signal includes delivering a source signal at a preselected frequency, and transducing the source signal to an acoustical signal within the chamber.

26. The method according to claim 25 wherein said sensing step includes transducing an acoustical signal to said sensed electrical signal.

27. The method according to claim 26 wherein said step for generating an acoustical signal includes providing a square wave signal, and filtering said square wave signal to generate a sine wave signal proportional to the square wave signal.

28. The method according to claim 27 wherein said step for generating an acoustical signal includes amplifying the sine wave signal generated after said filtering step.

29. The method according to claim 28 wherein said sensing step includes modulating said sensed signal and subsequently rectifying the signal after modulation.

30. The method according to the claim 29 wherein said measuring step includes receiving the same signal of said transducing step but rectifying said signal prior to said comparing step.

31. The method according to claim 30 further comprising the step of generating pulses of a fixed duration, said comparing step includes comparing said sensed signals and source signals during the fixed time duration of pulses generated during said pulse generating step.

32. The method according to claim 31 wherein said step of generating a source electrical signal includes sensing the phase change within the chamber and adjusting the frequency of the source electrical signal to minimize the phase change.

33. The method according to claim 32 wherein said step of sensing the phase change includes sensing said source signal and said sensed signal, comparing said signals and emitting a signal proportional to the signals sensed for adjusting the frequency of the source electrical signal to minimize the phase change.

34. The method according to claim 22 wherein the fibrous material includes insulation used in insulating wall space.

35. The method according to claim 34 further including the step of adding signals corresponding to the quantity of material within each chamber as each chamber passes said second station to provide a measure of the cumulative value of the quantity of fibrous material moved past the second station.

36. The method according to claim 34 further comprising the step of discharging said fibrous material from said chambers as each chamber is moved past said second station.

37. The method according to claim 36 wherein the chambers are moved along a closed path through the various stations for receiving the fibrous material, having the material in each chamber measured, and discharging the fibrous material after it has been measured.

38. An apparatus for measuring the quantity of material in a chamber comprising:
 (a) a chamber;
 (b) source means for generating an acoustical signal within the chamber including an oscillating means for delivering a source signal at a preselected frequency, a loud speaker communicating with said chamber for transducing the source signal to mechanical movement within the chamber, wherein said source means for generating an acoustical signal includes a source providing a square wave signal, a source filter for receiving a square wave signal and generating a sine wave proportional to the square wave signal received;
 (c) sensing means for sensing an acoustical signal from within said chamber, said sensing means including a microphone for transducing sound pressure to a sensed electrical signal corresponding to the magnitude of the acoustical signal sensed by the microphones;
 (d) a source electrical signal means for generating a source electrical signal corresponding to said acoustical signal; and
 (e) a logarithmic comparator including means for receiving said source electrical signal and comparing said source electrical signal received with the electrical signal generated by said sensing means and generating a signal proportional to the logarithm of the ratio of the signals corresponding to the quantity of material within said chamber.

39. The method for measuring the quantity of material in a chamber comprising:
  (a) generating an acoustical signal including delivering a source signal at a preselected frequency, and transducing a source signal to mechanical movement within the chamber, said step for generating an acoustical signal including providing a square wave signal, and filtering said square wave signal to generate a sine wave signal proportional to the square wave signal;
  (b) sensing the acoustical signal from within the chamber and transducing to a sensed electrical signal corresponding to the magnitude of acoustical signal sensed; and
  (c) generating a source electrical signal corresponding to said acoustical signal, receiving said source electrical signal and comparing said source electrical signal received with the electrical signal generated of said sensing step and generating a signal corresponding to the quantity of material within the chamber by generating a signal proportional to the logarithm of the ratio of signals corresponding to the source signal and the sensed signal.

40. An apparatus for measuring the thermal insulating value of a material passing a station comprising:
  (a) a source means for generating an acoustical signal at a said station;
  (b) a sensing means displaced from said source means for sensing the acoustical signal generated;
  (c) means for delivering the material to be sensed between said sensing means and said source means;
  (d) said sensing means including means for delivering a sensed electrical signal corresponding to the magnitude of the acoustical signal sensed by said sensing means;
  (e) means responsive to said sensed electrical signal for comparing the magnitude of the acoustical signal sensed by said sensing means to said acoustical signal generated by said source means, for measuring the attenuation of said acoustical signal generated by said source means and for calculating the thermal insulating value of material passing said station from a predetermined relationship of acoustical attenuation to thermal insulating value.

41. The apparatus according to claim 40 wherein said insulating value is the R value of the material passing the station.

42. The apparatus according to claim 41 wherein said means for calculating includes means for continually accumulating said insulating values to provide a total insulating value of the insulating material passing said station by summing the insulating values calculated for each acoustical signal sensed.

43. The apparatus according to claim 42 wherein said source means includes an impulse generator and a transducer for transducing an electrical signal produced by said impulse generator to an audio signal.

44. The apparatus according to claim 43 wherein said impulse generator includes a capacitor connected between said transducer and a power source, said capacitor being arranged to discharge to provide the impulse for operating the transmitting transducer to emit the audio signal.

45. The apparatus according to claim 44 wherein said means for calculating includes a computer and said sensing means includes a receiving transducer for converting an audio signal received to an electrical signal and delivering the electrical signal to said computer for calculating the "R" value corresponding to the signal sensed.

46. The apparatus according to claim 45 wherein said sensing means further includes a peak detector connected between the receiving transducer and said computer for delivering a signal to said computer upon detection of a peak value of the signal sensed.

47. The apparatus according to claim 46 wherein said computer is connected to the peak detector and to the impulse generator to control their operation during a selected time sequence, to receive information from the peak detector, and to provide an output corresponding to the insulating value based on the electrical signal sensed by the peak detector.

48. The apparatus according to claim 47 wherein said peak detector is an analog device, and further comprising an analog to digital converter to convert the analog signal from the peak detector to a digital signal in the form of a binary number for delivery to said computer.

49. The apparatus according to claim 48 further comprising an analog multiplexer located in series between the peak detector and the analog digital converter and controlled by the computer to select the signal received from the peak detector.

50. The apparatus according to claim 49 wherein an LCD display is connected to said computer for displaying information to the user.

51. The apparatus according to claim 50 wherein the apparatus includes a keyboard for inputing information into said computer, said input information including a selected insulation value.

52. The apparatus according to claim 51 further comprising a printer connected to the computer for printing out information related to the insulating value selected and the total insulating value actually delivered.

53. The apparatus according to claim 52 wherein said capacitor operates from a 60 volt source, said apparatus including a 12 to 60 volt converter to convert the energy from a 12 volt source to a 60 volt source for use by the capacitor, and further comprising a 5 volt regulator to regulate power from a 12 source to a 5 volt source for use by said computer, and a voltage converter for converting the 12 volt source to a plus and minus 24 volt source for use by said printer, said amplifier and said peak detector.

54. The apparatus according to claims 40, 41, 42, 43, or 44 wherein said means for delivering material includes a series of chambers for receiving material to be measured and means for moving said chambers past said station.

55. The apparatus according to claim 54 wherein said series of chambers are a fixed number of chambers arranged about a shaft for rotation, further comprising means for delivering material to each of said chambers as said chambers are rotated about said axis, and means for ejecting said material from said chamber as each chamber is rotated about said axis.

56. An apparatus for measuring the thermal insulating value of a material passing a station comprising:
  (a) an impulse generator connected to a transmitting transducer for generating an acoustical signal at a station corresponding to an electrical signal generated by said impulse generator;
  (b) a peak detector connected to a receiving transducer displaced from said source means for sensing the acoustical signal generated;
  (c) a series of chambers for delivering the material to be sensed between said transducers;

(d) said peak detector arranged for delivering a sensed electrical signal corresponding to the magnitude of the acoustical signal sensed by said receiving transducer;

(e) an electronic computer for receiving said sensed electrical signal from said peak detector;

(f) said computer including means for comparing the magnitude of the acoustical signal sensed by said receiving transducer to said acoustical signal generated by said transmitting transducer, for measuring the attenuation of said acoustical signal generated by said transmitting transducer and for calculating the thermal insulating value of material passing said station from a predetermined relationship of acoustical attenuation to thermal insulating value.

57. The apparatus according to claim 56 wherein said insulating value is the "R" value of the material passing said station.

58. The apparatus according to claim 57 wherein said computer includes means for accumulating said thermal insulating values to provide a total insulating value of the insulating material by summing the insulating values calculated for each acoustical signal sensed.

59. A method for measuring the thermal insulating value of a material passing a station comprising:

(a) generating an acoustical signal at a station;

(b) sensing the acoustical signal generated;

(c) delivering the material to be sensed past said station such that the material attenuates the acoustical signal before it is sensed;

(d) converting the sensed acoustical signal to a sensed electrical signal corresponding to the magnitude of the acoustical signal;

(e) comparing the magnitude of the acoustical signal sensed to the acoustical signal generated to measure the attenuation of the acoustical signal generated; and (f) calculating the thermal insulating value of material passing said station from a predetermined relationship of acoustical attenuation to thermal insulating value.

60. The method according to claim 59 wherein said insulating value is the R value of the material passing said station.

61. The method according to claim 60 further comprising the step of continually accumulating said insulating values to provide a total insulating value of the insulating material by summing the insulating value calculated for each acoustical signal sensed.

62. The method according to claim 61 wherein said generating step includes transducing an electrical impulse signal to an audio signal.

63. The method according to claim 62 wherein said sensing step includes converting an audio signal to an electrical signal for measuring the insulating value corresponding to the signal sensed.

64. The method according to claim 63 wherein said comparing step includes measuring the peak value of an analog signal and converting said analog signal to a digital signal.

65. The method according to claim 64 further comprising displaying a digital number corresponding to the sensed signal.

* * * * *